US00PP27704P3

(12) United States Plant Patent
Coakley

(10) Patent No.: US PP27,704 P3
(45) Date of Patent: Feb. 21, 2017

(54) ***DELPHINIUM* PLANT NAMED 'COADELBOL'**

(50) Latin Name: ***Delphinium* hybrid**
Varietal Denomination: Coadelbol

(71) Applicant: Anthony Paul Coakley, Glasgow (GB)

(72) Inventor: Anthony Paul Coakley, Glasgow (GB)

( * ) Notice: Subject to any disclaimer, the term of this patent is extended or adjusted under 35 U.S.C. 154(b) by 64 days.

(21) Appl. No.: 14/545,379

(22) Filed: Apr. 28, 2015

(65) Prior Publication Data

US 2016/0324057 P1 Nov. 3, 2016

(51) Int. Cl.
*A01H 5/02* (2006.01)

(52) U.S. Cl.
USPC ..... Plt./423

(58) Field of Classification Search
USPC ..... Plt./423
See application file for complete search history.

*Primary Examiner* — Keith Robinson
(74) *Attorney, Agent, or Firm* — Samuel R. McCoy, Jr.

(57) ABSTRACT

'Coadelbol' is a distinctive variety of *Delphinium* which is characterized by the combination of flowers with a large quantity of tepals and petaloids that exhibit a unique color combination of dark purple, blue and violet with pale yellow-green centers, an upright plant habit, a vigorous rate of growth, and the stability and uniformity of these traits through successive cycles of asexual propagation. The new cultivar produces a strong main flowering stem as well as a free and continuous bloom habit from early through late summer.

2 Drawing Sheets

Latin name of the genus and species: The Latin name of the genus and species of the novel variety disclosed herein is *Delphinium* hybrid.

Variety denomination: The inventive variety of *Delphinium* disclosed herein has been given the variety denomination 'Coadelbol'.

BACKGROUND OF THE INVENTION

The present invention relates to a new and distinct cultivar of *Delphinium*, which has been given the variety denomination of 'Coadelbol'. Its market class is PLT/423. The genus *Delphinium* is commonly known as a member of the Ranunculaceae family and may also be referred to as Larkspur. *Delphinium* plants bear inflorescences of a showy spike or racemes that may sometimes be paniculate and contain few to many flowers on erect and sometimes branching stems. The genus *Delphinium* is unusual in that all three primary colors are represented in different species. The tall hybrids with their long spikes are available in a wide range of colors including purple, mauve, pink, white, and cream as well as varying shades of blue. In Europe, they are grown as perennials but are treated as annuals in California and regions of similar climate.

Parentage: The *Delphinium* variety 'Coadelbol' is the result of a planned breeding program carried out in Glasgow, Scotland. 'Coadelbol' is a seedling selection which resulted from the controlled pollination of two proprietary *Delphinium* hybrid breeding accessions (unnamed, uncommercialized and undistributed) developed and owned by the inventor. The initial selection of the cultivar now known as 'Coadelbol' was made in August of 2008. At that time it was determined that said cultivar exhibited certain distinguishing characteristics that would prove favorable for commercial production and marketability.

Asexual Reproduction: 'Coadelbol' was first asexually propagated by tissue culture in 2012 at a tissue culture laboratory in Roelofarendsveen, The Netherlands under the control of the inventor. The distinctive characteristics of the inventive 'Coadelbol' cultivar are stable from generation to generation; clones of the cultivar produced by tissue culture maintain the distinguishing characteristics of the original plant.

SUMMARY OF THE INVENTION

The following characteristics have been repeatedly observed and represent the distinguishing characteristics of the new *Delphinium* cultivar 'Coadelbol'. These traits in combination distinguish 'Coadelbol' as a new and distinct cultivar.

1. *Delphinium* 'Coadelbol' exhibits a floret with a high tepal and petaloid count.
2. *Delphinium* 'Coadelbol' exhibits a unique color combination within the floret.
3. *Delphinium* 'Coadelbol' exhibits an upright growth habit.
4. *Delphinium* 'Coadelbol' exhibits a high degree of plant vigor.
5. *Delphinium* 'Coadelbol' exhibits a primary inflorescence with a strong peduncle.
6. *Delphinium* 'Coadelbol' exhibits a freely and continuous bloom habit.

BOTANICAL DESCRIPTION OF THE PLANT

Figure 1:
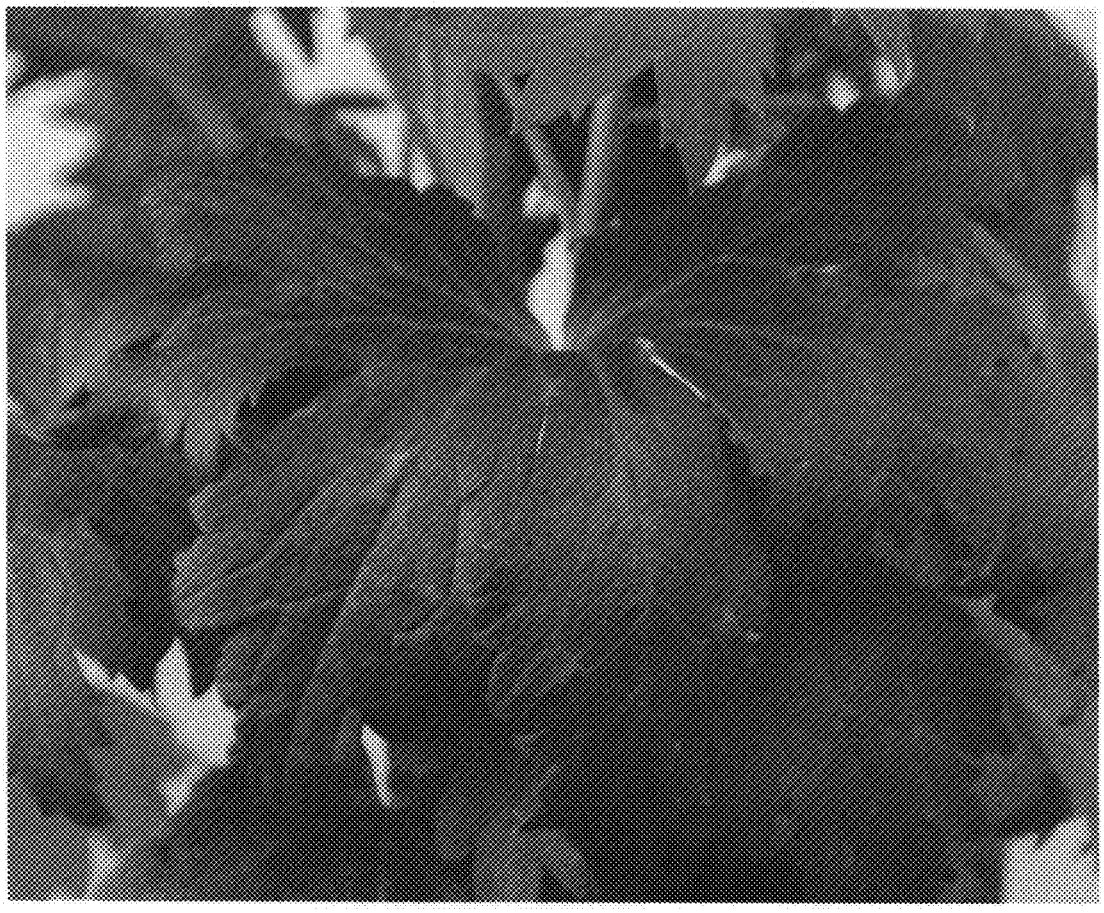
FIG. 1 shows, as nearly true as it is reasonably possible to make the same in color illustrations of this type, the foliage of the new cultivar, 'CoadelboL'. The plant shown was 9 months old and grown outdoors in Glasgow, Scotland using conventional production practices typically employed for producing *Delphinium* plants. No disease or pest measures were taken in producing this plant.
Figure 2:
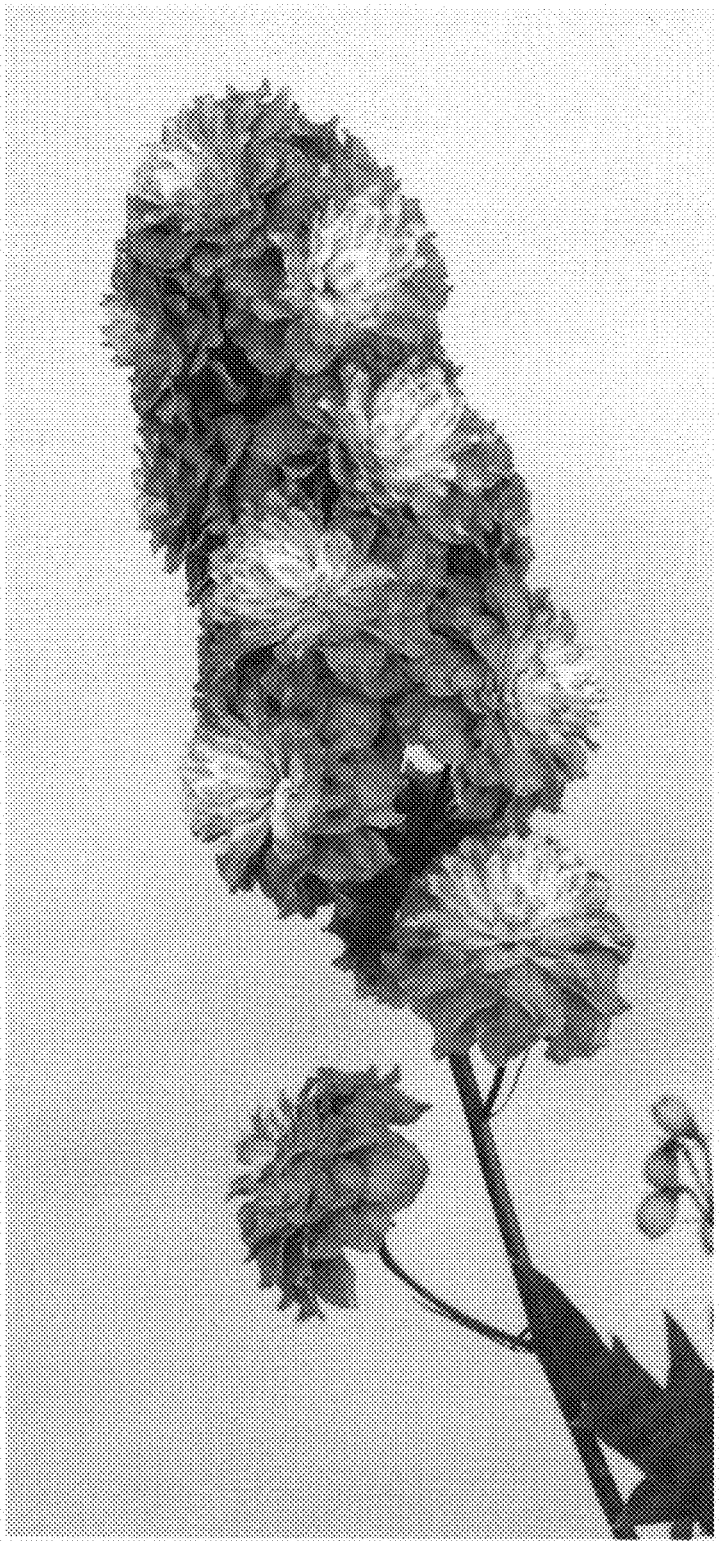
FIG. 2 shows, as nearly true as it is reasonably possible to make the same in color illustrations of this type, the inflorescence of 'Coadelbol'.

The following is a detailed botanical description of a new and distinct variety of *Delphinium* known as 'Coadelbol', based upon observations of a 9 month old plant grown outdoors in Glasgow, Scotland in a one liter nursery pot from winter to summer, using conventional production practices typically employed for producing *Delphinium* plants. No disease or pest measures were taken in producing this plant. Observation data was recorded in August of 2014.

Those skilled in the art will appreciate that certain characteristics will vary with older or, conversely, with younger plants. 'Coadelbol' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2007 edition.

A botanical description of 'Coadelbol' and comparisons with other varieties of *Delphinium* are provided below.

Technical Description of the Variety.

Plant description

- *Growth rate*.—Moderate.
- *Growth habit*.—Upright perennial flowering plant with flowers arranged on terminal racemes; numerous racemes per plant.
- *Height*.—Approximately 95.0 cm.
- *Width*.—Approximately 60.0 cm.
- *Environmental tolerances*.—Tolerates temperatures as low as 5 approximately minus 20 degrees Celsius (twenty degrees below freezing); upper temperature tolerance is unknown. No tolerance for drought.
- *Disease and pest resistance*.—Plants of the claimed plant have not been noted to be resistant to pathogens and pests common to *Delphinium*.
- *Propagation*.—Tissue culture.
- *Time to produce a rooted cutting*.—Approximately 4 to 5 weeks to produce a rooted cutting.

Root system: Fine, fibrous; freely branched and moderately dense.

Stem:

- *Branching habit*.—One primary flowering stem with no lateral branches.
- *Stem cross-section*.—Slightly to moderately quadrangulate.
- *Stem length*.—Approximately 50 cm, excluding the inflorescence.
- *Stem width*.—Approximately 0.1 cm.
- *Immature stem color*.—Yellow-green, near RHS 147A.
- *Mature stem color*.—Near RHS 143A, and covered with a very thin waxy layer, the color of which is near RHS 191D.
- *Color at internodes*.—Near RHS 143A, and covered with a very thin waxy layer, the color of which is near RHS 191D.
- *Stem pubescence*.—Base of stem is densely pubescent with short hairs of approximately 0.1 cm in length and colored white, near RHS NN155D; remainder of the stem is glabrous.
- *Stem texture*.—Smooth.
- *Stem luster*.—Matte.
- *Internode length*.—Approximately 1.9 cm.
- *Strength*.—Very strong.

Foliage:

- *Leaf arrangement*.—Alternate.
- *Leaf attachment*.—Petiolate.
- *Quantity of leaves per plant*.—Approximately 27 per main branch.
- *Leaf length*.—Average of 19 cm in length.
- *Leaf width*.—Average of 22 cm in width.
- *Leaf shape*.—Pedately lobed.
- *Leaf apex*.—Acute.
- *Leaf base*.—Hastate to strongly hastate.
- *Leaf margin*.—Biserrate.
- *Texture* (*adaxial surface*).—Glabrous; slightly glossy.
- *Texture* (*abaxial surface*).—Glabrous; slightly glossy.
- *Pubescence* (*adaxial surface*).—Absent.
- *Young leaf color* (*adaxial surface*).—Near RHS 143A to 143B.
- *Young leaf color* (*abaxial surface*).—Near RHS 143C.
- *Mature leaf color* (*adaxial surface*).—Near RHS N137A but slightly darker.
- *Mature leaf color* (*abaxial surface*).—Near RHS 147B.
- *Venation*.—Laciniate.
- *Vein color* (*adaxial surface*).—Near RHS 144A.
- *Vein color* (*abaxial surface*).—Near RHS 144A.
- *Petiole*.—Approximately 11.9 cm long and 0.45 cm wide; color is near 144A.

Inflorescence:

- *Inflorescence type*.—Terminal raceme.
- *Inflorescence dimensions*.—Approximately 44.1 cm long, as measured from the lowest flower to the apex of the inflorescence, and 9.1 cm wide.
- *Peduncle*.—Length — Approximately 41.0 cm. Diameter — Approximately 0.4 cm. Color — Green, near RHS 143A to 143B, but slightly darker. Attitude — Erect, in an average angle of 0 degrees to the main stem. Strength — Very Strong.
- *Bracts*.—Quantity — Two bracts are present at the base of each pedicel. Shape — Linear. Length — 1.4 cm, on average. Width — 0.1 cm, on average. Apex — Narrowly acute. Margin — Entire. Color (adaxial and abaxial surfaces) — Near RHS 143A.

Bud:

- *Flower bud shape*.—Obovate.
- *Flower bud length*.—1.3 cm, excluding the spur.
- *Flower bud diameter*.—Averaging 0.9 cm.
- *Bud color*.—Near RHS 94B to 94C, tinged near RHS 144B to 144C, with lower side colored near RHS 149D.

Flower:

- *Flowering quantity*.—About 90 buds and 98 fully opened flowers per lateral branch, at one time.
- *Natural flowering season*.—Midsummer to late summer.
- *Flower longevity on plant*.—Approximately three weeks.
- *Longevity as a cut flower*.—Approximately 7 days under high temperatures; approximately 14 days under cool temperature.

*Fragrance*.—Not fragrant.

*Pedicel*.—Length — Approximately 3.1 cm. Diameter — Approximately 1.5 mm. Texture — Smooth; glabrous. Color — Near RHS 143B and 144B.

*Perianth*.—Consisting of a spur, a single whorl of tepals and multiple whorls petaloids; the approximate diameter is 4.8 cm and the approximate depth is 2.7 cm, excluding the spur. Aspect of corolla is upward to slightly pendulous. Flowers are persistent. Tepal Description — Arrangement — Rotate. Quantity — Five. Length — Approximately 2.5 cm. Width — Two lower tepals average 1.6 cm and three upper tepals average 2.0 cm. Shape — Obovate. Margin — Entire, undulate. Apex — Broad acute. Texture — Glabrous, slightly glossy and slightly velvety. Aspect — Slightly curved backwards. Color, When Opening (adaxial surface) — Near RHS 99B to 99C; base and central stripe tinged near RHS 146C. Color, When Opening (abaxial surface) — Near RHS 98A and 99D; base and central stripe tinged near RHS 146B and 146C. Color, Fully Opened (adaxial surface) — Near RHS 99B; base and central stripe tinged near RHS 146C. Color, Fully Opened (abaxial surface) — Near RHS 98A and 99D; base and central stripe tinged near RHS 146B and 146C. Petaloid Description — Quantity — 15. Arrangement — Rotate. Length — Average: 2.1 cm. Width — Average: 1.2 cm. Shape — Obovate. Margin — Entire, undulate. Apex — Broad acute. Texture — Glabrous, slightly glossy, and slightly velvety. Aspect — Very slightly curved backwards. Color, When Opening (adaxial surface) — Near RHS NN155D, base and central stripe near RHS 145D, tip near RHS 94A. Color, When Opening (abaxial surface) — Near RHS NN155D, base and central stripe near RHS 145D, tip near RHS 94A. Color, Fully Opened (adaxial surface) — Near RHS 95C and 85A, base and central stripe near RHS 145B to 145D. Those petaloids near the center of the perianth are colored near RHS 157D, base, central stripe and tip near 145B to 145D. Color, Fully Opened (abaxial surface) — Near RHS 95C and 85A, base and central stripe near RHS 145B to 145D. Those petaloids near the center of the perianth are colored near RHS 157D, base, central stripe and tip near 145B to 145D.

*Spur*.—Shape — Oblong. Quantity per flower — 1. Length — Approximately 0.6 cm. Width — Approximately 0.3 cm. Margin — Entire. Texture — Glabrous, bullate. Color — Near RHS 146C, heavily tinged near RHS 94B to 94C.

Reproductive organs:

*Stamens*.—No stamens are present; all stamens are transformed into petaloids.

*Pistil*.—No pistils are present, all pistils are transformed into petaloids.

Seed and fruit: None observed.

COMPARISONS WITH THE PARENTS

Plants of the new cultivar 'Coadelbol' are similar to plants of the seed parent variety, an unnamed *Delphinium* hybrid, in most horticultural characteristics. However, flowers of the new variety have a higher tepal count with a stronger, unique and more consistent color.

Plants of the new cultivar 'Coadelbol' are similar to plants of the pollen parent variety, an unnamed *Delphinium* hybrid, in most horticultural characteristics. However, flowers of the new variety have a higher tepal count with a stronger, unique and more consistent color.

COMPARISONS WITH SIMILAR *DELPHINIUM* CULTIVARS KNOWN TO THE INVENTOR

Plants of the new cultivar 'Coadelbol' are similar to the cultivar, *Delphinium* 'Coadelcha' (co-pending U.S. Plant patent application Ser. No. 14/545,217). However, the claimed plant can be distinguished from 'Coadelcha' by several characteristics. A comparison of 'Coadelbol' with 'Coadelcha' is described in Chart 1.

CHART 1

| Characteristic | 'Coadelbol' | 'Coadelcha' |
|---|---|---|
| Color of main stem. | Green, near RHS 143A and 147B; covered with a thin, waxy layer colored greyed-green, near RHS 191D. | Near RHS 144A; heavily tinged near RHS N186C and covered by a thin, waxy layer colored greyed-green, near RHS 198A to 198C. |
| Color of peduncle. | Green, near RHS 143A to 143B, but slightly darker. | Yellow-green, near RHS 148A, but slightly darker. |
| Leaf length. | Longer than those of 'Coadelcha'. | Shorter than those of 'Coadelbol'. |
| Leaf width. | Wider than those of 'Coadelcha'. | More narrow than those of 'Coadelbol'. |
| Perianth diameter. | Smaller in diameter. | Larger in diameter. |
| Depth of perianth. | More shallow than the perianth of 'Coadelcha'. | Deeper than the perianth of 'Coadelbol'. |
| Tepal color when opening, adaxial surface. | Near RHS 98A and 99D; base and central stripe tinged near RHS 146B and 146C. | Near RHS 84D; base and central stripe near RHS 146C. |
| Tepal color when opening, abaxial surface. | Near RHS 98A and 99D; base and central stripe tinged near RHS 146B and 146C. | Near RHS 84C and 84D; base and central stripe near RHS 146C and a darker localized area or "dot" at the apex with color near RHS 146A. |
| Tepal color when fully open, adaxial surface. | Near RHS 99B; base and central stripe tinged near RHS 146C. | Near RHS 84D; base and central stripe near RHS 146C. |
| Tepal color when fully open, abaxial surface. | Near RHS 98A and 99D; base and central stripe tinged near RHS 146B and 146C. | Near RHS 84C and 84D; base and central stripe near RHS 146C and a darker localized area or "dot" at the apex with color near RHS 146A. |
| Petaloid color when fully open, adaxial surface. | Near RHS 95C and 85A, base and central stripe near RHS 145B to 145D. Those petaloids near the center of the perianth are colored near RHS 157D, base, central stripe and tip near 145B to 145D. | Near RHS Purple 77B, 78D and Blue 100A mixed with Yellow-Green 144A and 145A. |
| Petaloid color when fully open, abaxial surface. | Near RHS 95C and 85A, base and central stripe near RHS 145B to 145D. Those petaloids near the center of the perianth are colored near RHS 157D, base, central stripe and tip near 145B to 145D. | Near RHS 77B, 78D and Blue 100A, mixed with Yellow-Green 144A and 145A. |

Plants of the new cultivar 'Coadelbol' are also similar to the cultivar, *Delphinium* 'Coadelfla' (co-pending U.S. Plant patent application Ser. No. 14/545,380). However, the claimed plant can be distinguished from 'Coadelfla' by several characteristics. A comparison of 'Coadelfla' with 'Coadelbol' is described in Chart 2.

CHART 2

| Characteristic | 'Coadelbol' | 'Coadelfla' |
|---|---|---|
| Color of main stem. | Green, near RHS 143A and 147B; covered with a thin, waxy layer colored greyed-green, near RHS 191D. | Near RHS 146A to 146B and covered with a thin, waxy layer colored yellow-green, near RHS 147C to 147D. |
| Color of peduncle. | Green, near RHS 143A to 143B, but slightly darker. | Yellow-green, near RHS 148A. |
| Leaf length. | Longer than those of 'Coadelfla'. | Shorter than those of 'Coadelbol'. |
| Leaf width. | Wider than those of 'Coadelfla'. | More narrow than those of 'Coadelbol'. |
| Perianth diameter. | Smaller in diameter. | Larger in diameter. |
| Tepal color when opening, adaxial surface. | Near RHS 98A and 99D; base and central stripe tinged near RHS 146B and 146C. | Near RHS 76A; the base and also a darker localized area or "dot" at the apex with color near RHS 146A to 146B. |
| Tepal color when opening, abaxial surface. | Near RHS 98A and 99D; base and central stripe tinged near RHS 146B and 146C. | Slightly lighter than RHS N77D; the base and also a darker localized area or "dot" at the apex with color near RHS 146A. |
| Tepal color when fully open, adaxial surface. | Near RHS 99B; base and central stripe tinged near RHS 146C. | Near RHS 99B; base and central stripe tinged near RHS 146C. |
| Tepal color when fully open, abaxial surface. | Near RHS 98A and 99D; base and central stripe tinged near RHS 146B and 146C. | Near RHS 98A and 99D; base and central stripe tinged near RHS 146B and 146C. |
| Petaloid color when fully open, adaxial surface. | Near RHS 95C and 85A, base and central stripe near RHS 145B to 145D. Those petaloids near the center of the perianth are colored near RHS 157D, base, central stripe and tip near 145B to 145D. | Near RHS 76A; the base and also a darker localized area or "dot" at the apex with color near RHS 146A to 146B. |
| Petaloid color when fully open, abaxial surface. | Near RHS 95C and 85A, base and central stripe near RHS 145B to 145D. Those petaloids near the center of the perianth are colored near RHS 157D, base, central stripe and tip near 145B to 145D. | Slightly lighter than RHS N77D; the base and also a darker localized area or "dot" at the apex with color near RHS 146A. |

That which is claimed is:

1. A new and distinct variety of *Delphinium* plant named 'Coadelbol', substantially as described and illustrated herein.

* * * * *